United States Patent [19]

Baumann et al.

[11] Patent Number: 5,703,017
[45] Date of Patent: Dec. 30, 1997

[54] 3-(HET) ARYLCARBOXYLIC ACID DERIVATIVES, THEIR PREPARATION AND INTERMEDIATES FOR THEIR PREPARATION

[75] Inventors: Ernst Baumann, Dudenhofen; Joachim Rheinheimer; Uwe Josef Vogelbacher, both of Ludwigshafen; Matthias Bratz, Speyer; Hans Theobald; Matthias Gerber, both of Limburgerhof; Karl-Otto Westphalen, Speyer; Helmut Walter, Obrigheim; Wilhelm Rademacher, Limburgerhof, all of Germany

[73] Assignee: BASF Aktiengesellschaft, Ludwigshafen, Germany

[21] Appl. No.: 537,843

[22] PCT Filed: Apr. 13, 1994

[86] PCT No.: PCT/EP94/01141

§ 371 Date: Oct. 19, 1995

§ 102(e) Date: Oct. 19, 1995

[87] PCT Pub. No.: WO94/25442

PCT Pub. Date: Nov. 10, 1994

[30] Foreign Application Priority Data

Apr. 23, 1993 [DE] Germany .................. P 43 13 412.2

[51] Int. Cl.⁶ .................. A01N 43/54; A01N 43/66; C07D 239/60; C07D 251/30; C07D 409/12; C07D 401/12; C07D 405/12; C07C 69/734

[52] U.S. Cl. .................. 504/227; 504/228; 504/230; 504/239; 504/240; 504/241; 504/242; 504/243; 544/219; 544/235; 544/242; 544/253; 544/319; 546/340; 546/341; 548/204; 548/248; 548/341.5; 548/376.1; 549/79; 549/498; 549/499; 562/426; 562/470; 568/41; 568/425; 568/496

[58] Field of Search .................. 504/227, 228, 504/230, 239, 240, 241, 242, 243; 544/219, 235, 253, 319, 242; 546/340, 341; 548/204, 248, 341.5, 376.1; 549/79, 498, 499; 562/426, 470; 568/41, 425, 496

[56] References Cited

U.S. PATENT DOCUMENTS

| | | | |
|---|---|---|---|
| 5,178,663 | 1/1993 | Harada et al. | 504/242 |
| 5,270,289 | 12/1993 | Harde et al. | 504/243 |
| 5,326,744 | 7/1994 | Rheinheimer et al. | 504/241 |

FOREIGN PATENT DOCUMENTS

| | | |
|---|---|---|
| 347 811 | 12/1989 | European Pat. Off. |
| 400 741 | 12/1990 | European Pat. Off. |
| 409 368 | 1/1991 | European Pat. Off. |
| 481 512 | 4/1992 | European Pat. Off. |
| 517 215 | 12/1992 | European Pat. Off. |
| 548 710 | 6/1993 | European Pat. Off. |

OTHER PUBLICATIONS

Chemical Abstracts vol. 119, 1993, No. 13, Ab 119:139254e.
Chemical Abstracts, vol. 85, No. 5, Aug. 2, 1976, Ab:85:32649a.
Agr. Biol. Chem. 40(5),933–1000,1976, On the Sterochemistry . . . Kogure et al.
Advanced Organic Chem., Third Ed., Jerry March 1985, pp. 750, 863.
Bul.Chem Soc. of Japan, vol. 49(1), 341–342,1976, Photochemical Reaction . . . Chung et al.

Primary Examiner—S. Mark Clardy
Attorney, Agent, or Firm—Keil & Weinkauf

[57] ABSTRACT

3-(Het)arylcarboxylic acid derivatives of the formula I

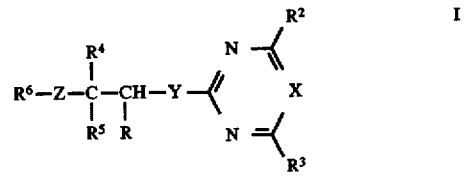

where R is formyl, $CO_2H$ or a radical hydrolyzable to COOH and the other substituents have the following meanings:

$R^2$ and $R^3$ are each halogen, alkyl, haloalkyl, alkoxy, haloalkoxy or alkylthio;

X is nitrogen or $CR^{14}$, where $R^{14}$ is hydrogen or, together with $R^3$, forms an alkylene or alkenylene chain, in each of which a methylene group is replaced by oxygen;

$R^4$ is phenyl or naphthyl, each of which is unsubstituted or substituted or an unsubstituted or substituted five-membered or six-membered heteroaromatic structure containing one to three nitrogen atoms or one sulfur or oxygen atom;

$R^5$ is hydrogen, alkyl, alkenyl, alkynyl, cycloalkyl, haloalkyl, alkoxyalkyl, alkylthioalkyl or phenyl;

$R^6$ is $C_1$–$C_8$-alkyl, $C_3$–$C_6$-alkenyl, $C_3$–$C_6$-alkynyl or $C_3$–$C_4$-cyclo-alkyl, each of which may be mono- or polysubstituted;

Y is sulfur, oxygen or a single bond; and

Z is sulfur or oxygen;

with the proviso that $R^6$ is not unsubstituted $C_1$–$C_4$-alkyl when $R^4$ is unsubstituted phenyl, Z is oxygen and simultaneously $R^5$ is methyl or hydrogen.

14 Claims, No Drawings

3-(HET)ARYLCARBOXYLIC ACID DERIVATIVES, THEIR PREPARATION AND INTERMEDIATES FOR THEIR PREPARATION

This application has been filed under 35 USC 371 as a national stage application of PCT/EP94/01141, filed Apr. 13, 1994.

BACKGROUND OF THE INVENTION 3-(het)arylcarboxylic acid derivatives of the general formula I

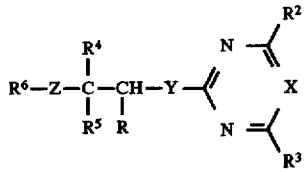

where R is formyl, $CO_2H$ or a radical hydrolyzable to COOH, and the other substituents have the following meanings:

$R^2$ is halogen, $C_1-C_4$-alkyl, $C_1-C_4$-haloalkyl, $C_1-C_4$-alkoxy, $C_1-C_4$-haloalkoxy or $C_1-C_4$-alkylthio;

X is nitrogen or $CR^{14}$, where $R^{14}$ is hydrogen or, together with $R^3$, forms a 3-membered or 4-membered alkylene or alkenylene chain, in each of which a methylene group is replaced by oxygen;

$R^3$ is halogen, $C_1-C_4$-alkyl, $C_1-C_4$-haloalkyl, $C_1-C_4$-alkoxy, $C_1-C_4$-haloalkoxy or $C_1-C_4$-alkylthio or $R^3$ is linked to $R^{14}$ as stated above to form a 5-membered or 6-membered ring;

$R^4$ is phenyl or naphthyl which may be substituted by one or more, in particular one to three of the following radicals: halogen, nitro, cyano, hydroxyl, mercapto, amino, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-alkylamino, di-$C_1-C_4$-alkylamino, $C_1-C_4$-alkylcarbonyl or $C_1-C_4$-alkoxycarbonyl;

a five-membered or six-membered heteroaromatic structure which contains one to three nitrogen atoms and/or one sulfur or oxygen atom and may carry one or more of the following radicals: halogen, nitro, cyano, hydroxyl, mercapto, amino, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-alkylamino, $C_1-C_4$-dialkylamino, $C_1-C_4$-alkylcarbonyl, $C_1-C_4$-alkoxycarbonyl or phenyl;

$R^5$ is hydrogen, $C_1-C_4$-alkyl, $C_3-C_6$-alkenyl, $C_3-C_6$-alkynyl, $C_3-C_8$-cycloalkyl, $C_1-C_4$-haloalkyl, $C_1-C_4$-alkoxyalkyl, $C_1-C_4$-alkylthioalkyl or phenyl;

$R^6$ is $C_1-C_8$-alkyl, $C_3-C_6$-alkenyl, $C_3-C_6$-alkynyl or $C_3-C_8$-cycloalkyl, it being possible for these radicals to be mono- or polysubstituted in each case by: halogen, nitro, cyano, $C_1-C_4$-alkoxy, $C_3-C_6$-alkenyloxy, $C_3-C_6$-alkynyloxy, $C_1-C_4$-alkylthio, $C_1-C_4$-haloalkoxy, $C_1-C_4$-alkylcarbonyl, $C_1-C_4$-alkoxycarbonyl, $C_1-C_4$-alkylamino, di-$C_1-C_4$-alkylamino, phenyl or phenyl or phenoxy which is mono- or polysubstituted; for example mono- to trisubstituted, by halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

Y is sulfur or oxygen or a single bond; and

Z is sulfur or oxygen;

with the proviso that $R^6$ is not unsubstituted $C_1-C_4$-alkyl when $R^4$ is unsubstituted phenyl, Z is oxygen and simultaneously $R^5$ is methyl or hydrogen.

The prior art, eg. EP-A 347 811, EP-A 400 741, EP-A 409 368, EP-A 481 512, EP-A 517 215, Chemical Abstracts, 119, No. 139 254e (1993), and the prior German application P 41 42 570 (EP-A-548 710), describes similar carboxylic acid derivatives, including 3-alkoxy derivatives but not those which carry a het(aryl) radical in the 3 position.

SUMMARY OF THE INVENTION

Since the herbicidal and/or bioregulatory action and selectivity of the known compounds is not always satisfactory, it is an object of the present invention to provide compounds having better selectivity and/or better biological activity.

We have found that this object is achieved and that the 3-(het)arylcarboxylic acid derivatives defined at the outset have excellent herbicidal and plant growth-regulating properties. Furthermore, the compounds I have good pharmacological efficacy, particularly in the cardiovascular sector.

The preparation of the novel compounds starts from the epoxides IV, which are obtained in a generally known manner, as described, for example, in J. March, Advanced Organic Chemistry, 2nd ed., 1983, page 862 and page 750, from the aldehydes or ketones II or the olefins III:

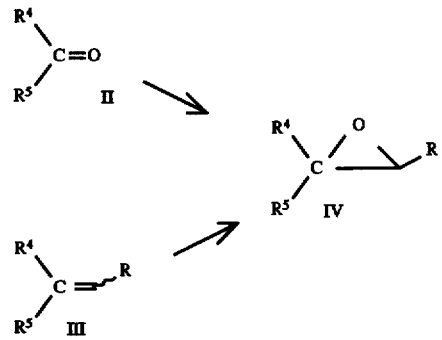

3-(Het)arylcarboxylic acid derivatives of the general formula VI can be prepared by reacting the epoxide of the general formula IV (for example, with R=ROOR$^{10}$) with alcohols or thiols of the general formula V, where $R^6$ and Z have the meanings stated in claim 1.

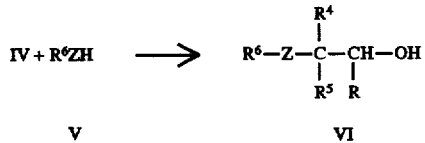

For this purpose, compounds of the general formula IV are heated with an excess of the compounds of the formula V, for example with 1.2–7, preferably 2–5, mole equivalents, to 50°–200° C., preferably 80°–150° C.

The reaction can also be carried out in the presence of a diluent. All solvents which are inert to the reagents used may be employed for this purpose.

Examples of such solvents or diluents are water, aliphatic, alicyclic and aromatic hydrocarbons, each of which may be chlorinated, for example hexane, cyclohexane, petroleum ether, naphtha, benzene, toluene, xylene, methylene chloride, chloroform, carbon tetrachloride, ethylene chloride and trichloroethylene, ethers, such as diisopropyl ether, dibutyl ether, propylene oxide, dioxane and tetrahydrofuran, ketones, for example acetone, methyl ethyl ketone, methyl isopropyl ketone and methyl isobutyl ketone, nitriles, such as acetonitrile and propionitrile, alcohols, such as methanol, ethanol, isopropanol, butanol and ethylene glycol, esters, for example ethyl acetate and amyl acetate, amides, such as dimethylformamide and dimethylacetamide, sulfoxides and sulfones, fox example dimethyl sulfoxide and sulfolane, and bases, such as pyridine.

The reaction is preferably carried out at from 0° C. to the boiling point of the solvent or solvent mixture.

The presence of a catalyst for the reaction may be advantageous. Suitable catalysts are strong organic and inorganic acids and Lewis acids. Examples of these include sulfuric acid, hydrochloric acid, trifluoroacetic acid, boron trichloride etherate and titanium(IV) alcoholates.

The novel compounds in which Y is oxygen and the remaining substituents have the meanings stated under the general formula I can be prepared, for example, by reacting the 3-(het)arylcarboxylic acid derivatives of the general formula VI in which the substituents have the stated meanings with compounds of the general formula VII

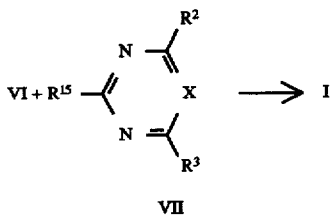

VII where $R^{15}$ is halogen or $R^{16}$—$SO_2$— and $R^{16}$ may be $C_1$–$C_4$-alkyl, $C_1$–$C_4$-haloalkyl or phenyl. The reaction is preferably carried out in one of the abovementioned inert diluents with the addition of a suitable base, ie. a base which effects deprotonation of the intermediate VI, at from room temperature to the boiling point of the solvent.

The bases may be an alkali metal or alkaline earth metal hydride, such as sodium hydride, potassium hydride or calcium hydride, a carbonate, such as an alkali metal carbonate, for example, sodium carbonate or potassium carbonate, an alkali metal or alkaline earth metal hydroxide, such as sodium hydroxide or potassium hydroxide, an organometallic compound, such as butyllithium, or an alkali metal amide, such as lithium diisopropylamide.

The novel compounds in which Y is sulfur and the remaining substituents have the meanings stated under the general formula I can be prepared, for example, by reacting 3-(het)arylcarboxylic acid derivatives of the general formula VIII, which are obtainable in a known manner from compounds of the general formula VI and in which the substituents have the abovementioned meanings, with compounds of the general formula IX where $R^2$, $R^3$ and X have the meanings stated under the general formula I.

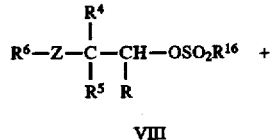

VIII

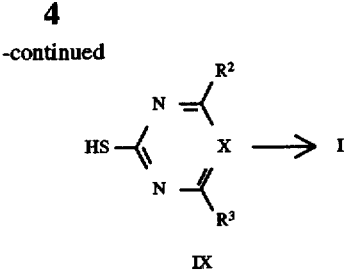

IX

The reaction is preferably carried out in one of the abovementioned inert diluents with the addition of a suitable base, ie. a base which effects deprotonation of the intermediate IX, at from room temperature to the boiling point of the solvent.

The bases used may be organic bases, such as tertiary amines, for example triethylamine, pyridine, imidazole or diazabicyclo-undecene, in addition to the abovementioned bases.

Compounds of the formula I can also be prepared by starting from the corresponding carboxylic acids, ie. compounds of the formula I in which $R^1$ is hydroxyl, and first converting these in a conventional manner into an activated form, such as a halide, an anhydride or an imidazolide, and then reacting this with a corresponding hydroxyl compound $HOR^{10}$. This reaction can be carried out in the conventional solvents and often requires the addition of a base, the abovementioned bases being suitable. These two steps can also be simplified, for example, by allowing the carboxylic acid to act on the hydroxy compound in the presence of a water-eliminating agent, such as a carbodiimide.

In addition, compounds of the formula I can also be prepared by starting from the salts of the corresponding carboxylic acids, ie. from compounds of the formula I in which R is $COR^1$ and $R^1$ is OM, where M may be an alkali metal cation or one equivalent of an alkaline earth metal cation. These salts can be reacted with many compounds of the formula $R^1$-A, where A is a conventional nucleofugic leaving group, for example halogen, such as chlorine, bromine or iodine, or aryl- or alkylsulfonyl which is unsubstituted or substituted by halogen, alkyl or haloalkyl, eg. toluenesulfonyl and methylsulfonyl, or another equivalent leaving group. Compounds of the formula $R^1$-A having a reactive substituent A are known or can be readily obtained on the basis of general technical knowledge. The reaction can be carried out in the conventional solvents and is effected advantageously with the addition of a base, the abovementioned bases being suitable.

R in the formula I can be widely varied. For example, R is a group $$\overset{O}{\underset{}{\overset{\parallel}{C}}}-R^1$$

where $R^1$ has the following meanings:
a) hydrogen,
b) a succinylimidoxy group;
c) a 5-membered heteroaromatic structure which is bonded via a nitrogen atom, such as pyrrolyl, pyrazolyl, imidazolyl or triazolyl, and which may carry one or two halogen atoms, in particular fluorine or chlorine and/or one or two of the following radicals:
$C_1$–$C_4$-alkyl, such as methyl, ethyl, 1-propyl, 2-propyl, 2-methyl-2-propyl, 2-methyl-1-propyl, 1-butyl or 2-butyl;

$C_1$–$C_4$-haloalkyl, in particular $C_1$- or $C_2$-haloalkyl, for example fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trifluoroethyl or pentafluoroethyl;

$C_1$–$C_4$-haloalkoxy, in particular $C_1$- or $C_2$-haloalkoxy, such as difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy;

$C_1$–$C_4$-alkylthio, such as methylthio, ethylthio, propylthio, 1-methylethylthio, butylthio, 1-methylpropylthio, 2-methyl-propylthio or 1,1-dimethylethylthio, in particular methylthio or ethylthio;

d) $R^1$ is furthermore a radical

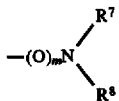

where m is 0 or 1 and $R^7$ and $R^8$ may be identical or different and have the following meanings:

hydrogen;

$C_1$–$C_8$-alkyl, in particular $C_1$–$C_4$-alkyl as tested above;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-3-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl;

$C_3$–$C_8$-cycloalkyl, such as cyclopropyl, cyclobutyl, cyclopentyl, cyclohexyl or cycloheptyl, cyclooctyl, where these alkyl, cycloalkyl, alkenyl and alkynyl groups may each carry one to five halogen atoms, in particular fluorine or chlorine, and/or one or two of the following groups:

$C_1$–$C_4$-alkyl, $C_1$–$C_4$-alkoxy, $C_1$–$C_4$-alkylthio, $C_1$–$C_4$-haloalkoxy as stated above, $C_3$–$C_6$-alkenyloxy, $C_3$–$C_6$-alkenylthio, $C_3$–$C_6$-alkynyloxy, or $C_3$–$C_6$-alkynylthio, where the alkenyl and alkynyl moieties present in these radicals preferably have the abovementioned meanings;

$C_1$–$C_4$-alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$–$C_4$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl;

$C_3$–$C_6$-alkenylcarbonyl, $C_3$–$C_6$-alkynylcarbonyl, $C_3$–$C_6$-alkenyloxycarbonyl or $C_3$–$C_6$-alkynyloxycarbonyl, where the alkenyl and alkynyl radicals are preferably defined as stated individually above;

phenyl, unsubstituted or monosubstituted or polysubstituted, for example monosubstituted to trisubstituted, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, for example 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl or 2,6-difluorophenyl;

di-$C_1$–$C_4$-alkylamino, in particular dimethylamino, dipropylamino, N-propyl-N-methylamino, N-propyl-N-ethylamino, diisopropylamino, N-isopropyl-N-methylamino, N-isopropyl-N-ethylamino or N-isopropyl-N-propylamino;

$R^7$ and $R^8$ are each furthermore phenyl, which may be substituted by one or more, for example one to three, of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, as stated in particular above;

or $R^7$ and $R^8$ together form a cyclic, optionally substituted, for example $C_1$–$C_4$-alkyl-substituted, $C_4$–$C_7$-alkylene chain which may contain a heteroatom selected from the group consisting of oxygen, sulfur and nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_2)_3$—, —NH—$(CH_2)_3$—, —$CH_2$—NH—$(CH_2)_2$—, —$CH_2$—CH=CH—$CH_2$— or —CH=CH—$(CH_2)_3$—;

e) $R^1$ is furthermore a group

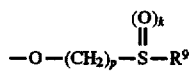

where k is 0, 1 or 2, p is 1, 2, 3 or 4 and $R^9$ is
$C_1$–$C_4$-alkyl, $C_1$–$C_4$-haloalkyl, $C_3$–$C_6$-alkenyl, $C_3$–$C_6$-alkynyl or unsubstituted or substituted phenyl, as stated in particular above.

f) $R^1$ is furthermore a radical $OR^{10}$, where $R^{10}$ is:

hydrogen, the cation of an alkali metal, such as lithium, sodium or potassium, or the cation of an alkaline earth metal, such as calcium, magnesium or barium, or an environmentally compatible organic ammonium ion, such as tertiary $C_1$–$C_4$-alkylammonium or the ammonium ion;

$C_3$–$C_8$-cycloalkyl as stated above, which may carry one to three $C_1$–$C_4$-alkyl groups;

$C_1$–$C_8$-alkyl, in particular methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which may carry one to five halogen atoms, in particular fluorine or chlorine, and/or one of the following radicals:

$C_1$–$C_4$-alkoxy, $C_1$–$C_4$-alkylthio, cyano, $C_1$–$C_4$-alkylcarbonyl, $C_3$–$C_8$-cycloakyl [sic], $C_1$–$C_4$-alkoxycarbonyl, phenyl, phenoxy or phenylcarbonyl, where the aromatic radicals in turn may each carry one to five halogen atoms and/or one to three of the following radicals: nitro, cyano, $C_1$–$C_4$-alkyl, $C_1$–$C_4$-haloaklyl $C_1$–$C_4$-alkoxy, $C_1$–$C_4$-haloalkoxy and/or $C_1$–$C_4$-alkylthio, as stated in particular above;

$C_1$–$C_8$-alkyl as stated above, which may carry one to five halogen atoms, in particular fluorine and/or chlorine, and carries one of the following radicals: a 5-membered heteroaromatic structure which contains one to three nitrogen atoms, or a 5-membered heteroaromatic structure which contains one nitrogen atom and one oxygen or sulfur atom and which may carry one to four halogen atoms and/or one or two of the following radicals:

nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular examples are: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5-yl, 3-tert-butylisoxazol-5-yl;

$C_2$–$C_6$-alkyl which carries one of the following radicals in the 2 position: $C_1$–$C_4$-alkoxyimino, $C_3$–$C_6$-alkynyloxyimino, $C_3$–$C_6$-haloalkenyloxyimino or benzyloxyimino;

$C_3$–$C_6$-alkenyl or $C_3$–$C_6$-alkynyl, where these groups in turn may carry one to five halogen atoms;

$R^{10}$ is furthermore phenyl which may carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, as stated in particular above;

a 5-membered heteroaromatic structure which is bonded via a nitrogen atom, contains one to three nitrogen atoms and may carry one or two hydrogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular examples are 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl1,2,4-triazol-1-yl, 1-benzotriazolyl and 3,4-dichloroimidazol-1-yl;

$R^{10}$ is furthermore a group

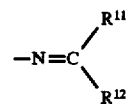

where $R^{11}$ and $R^{12}$ may be identical or different and are each:

$C_1$–$C_8$-alkyl, $C_3$–$C_6$-alkenyl, $C_3$–$C_6$-alkynyl or $C_3$–$C_8$-cycloalkyl, where these radicals may carry $C_1$–$C_4$-alkoxy, $C_1$–$C_4$-alkylthio and/or unsubstituted or substituted phenyl, as stated in particular above;

phenyl, which may be substituted by one or more, for example one to three, of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, where these radicals correspond in particular to the abovementioned ones;

or $R^{11}$ and $R^{12}$ together form a $C_3$–$C_{12}$-alkylene chain which may carry one-to three $C_1$–$C_4$-alkyl groups and may contain a heteroatom selected from the group consisting of oxygen, sulfur and nitrogen, as stated in particular for $R^7$ and $R^8$.

g) $R^1$ is furthermore a radical

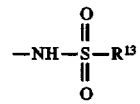

where $R^{13}$ is:

$C_1$–$C_4$-alkyl, $C_3$–$C_6$-alkenyl, $C_3$–$C_6$-alkynyl, $C_3$–$C_8$-cycloalkyl as stated in particular above, where these radicals may carry $C_1$–$C_4$-alkoxy, $C_1$–$C_4$-alkylthio and/or phenyl as stated above;

phenyl, unsubstituted or substituted, in particular as stated above.

With regard to the biological activity, preferred 3-(het) aryl-oxy(thio)carboxylic acid derivatives are those of the general formula I in which the substituents have the following meanings:

$R^2$ is one of the $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio groups stated individually in the case of $R^1$ or is halogen, in particular chlorine, methyl, methoxy, ethoxy, difluoromethoxy, trifluoromethoxy or particularly preferably methoxy;

X is nitrogen or $CR^{14}$, where $R^{14}$ is hydrogen or, together with $R^3$, forms a 4-membered or 5-membered alkylene or alkenylene chain, in each of which a methylene group is replaced by oxygen, such as —$CH_2$—$CH_2$—O—, —CH=CH—O—, —$CH_2$—$CH_2$—$CH_2$—O— or —CH=CH—$CH_2$O— [sic], in particular hydrogen or —$CH_2$—$CH_2$—O—;

$R^3$ is one of the $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio groups stated in the case of $R^1$ or is halogen, in particular chlorine, methyl, methoxy, ethoxy, difluoromethoxy, trifluoromethoxy or is bonded to $R^{14}$ as stated above to form a 5-membered or 6-membered ring, $R^3$ is particularly preferably methoxy;

$R^4$ is 5-membered or 6-membered heteroaryl, such as furyl, thienyl, pyrryl, pyrazolyl, imidazolyl, triazolyl, isoxazolyl, oxazolyl, isothiazolyl, thiazolyl, thiadiazolyl, pyridyl, pyrimidinyl, pyrazinyl, pyridazinyl, triazinyl, for example 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrrolyl, [sic] 3-pyrazolyl, 4-pyrazolyl, 5-pyrazolyl, 2-pyridyl, 3-pyridyl, 4-pyridyl, oxa-2,4-diazolyl, oxa-3,4-diazoylyl [sic], thia-2,4-diazolyl, thia-3,4-diazolyl or triazolyl, where the heteroaromatic structures may carry one to five halogen atoms as stated above, in particular fluorine or chlorine and/or one to three of the following radicals:

$C_1$-$C_4$-alkyl, $C_1$-$C_4$-alkoxy, $C_1$-$C_4$-alkylthio, cyano, nitro, $C_1$-$C_8$-alkylcarbonyl, $C_1$-$C_8$-alkoxycarbonyl, phenyl, phenoxy or phenylcarbonyl as stated in general and in particular above;

$R^4$ is furthermore phenyl or naphthyl, each of which may be substituted by one or more, eg. one to three, of the following radicals: halogen, nitro, cyano, hydroxyl, mercapto, amino, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylamino or di-$C_1$-$C_4$-alkylamino, $C_1$-$C_4$-alkylcarbonyl, $C_1$-$C_4$-alkoxycarbonyl, in particular as stated in the case of $R^7$ and $R^8$ or for example 3-hydroxyphenyl, 4-dimethylaminophenyl, 2-mercaptophenyl, 3-methoxycarbonylphenyl, 4-acetylphenyl, 1-naphthyl, 2-naphthyl, 3-bromo-2-naphthyl, 4-methyl-1-naphthyl, 5-methoxy-1-naphthyl, 6-trifluoromethyl-1- naphthyl [sic], 7-chloro-1-naphthyl or 8-hydroxy-1-naphthyl;

$R^5$ is hydrogen, $C_1$-$C_4$-alkyl, $C_3$-$C_6$-alkenyl, $C_3$-$C_6$-alkynyl, $C_3$-$C_7$-cycloalkyl, $C_1$-$C_4$-haloalkyl, $C_1$-$C_4$-alkoxyalkyl, $C_1$-$C_4$-alkylthioalkyl or phenyl as stated above in particular for $R_4$;

$R^6$ is $C_1$-$C_8$-alkyl, $C_3$-$C_6$-alkenyl, $C_3$-$C_6$-alkynyl or $C_3$-$C_8$-cycloalkyl as stated in particular above, each of which may be mono- to polysubstituted by the following radicals: halogen, nitro, cyano, $C_1$-$C_4$-alkoxy, $C_3$-$C_6$-alkenyloxy, $C_3$-$C_6$-alkynyloxy, $C_1$-$C_4$-alkylthio, $C_1$-$C_4$-haloalkoxy, $C_1$-$C_4$-alkylcarbonyl, $C_1$-$C_4$-alkoxycarbonyl, $C_1$-$C_4$-alkylamino or di-$C_1$-$C_4$-alkylamino or unsubstituted or substituted phenyl or phenoxy, as stated in particular above;

Y is sulfur, oxygen or a single bond and

Z is sulfur or oxygen, with the proviso that $R^6$ is not unsubstituted $C_1$-$C_4$-alkyl when $R^4$ is unsubstituted phenyl, Z is oxygen and simultaneously $R^5$ is methyl or hydrogen.

Compounds of the formula I where $R^2$ and $R^3$ are each methoxy and X is CH are particularly preferred. Examples of preferred compounds are listed in the following table. The definitions given for $R^4$ there and in Tables 1 and 2 are likewise to be regarded as preferred, irrespective of the definitions of radicals in combination with $R^4$.

TABLE

| $R^1$ | $R^4$ | $R^5$ | $R^6$ | $R^2$ | $R^3$ | X | Y | Z |
|---|---|---|---|---|---|---|---|---|
| OH | Phenyl | Methyl | Methyl | $OCH_3$ | $OCH_3$ | CH | S | S |
| OH | Phenyl | Methyl | Methyl | $OCH_3$ | $OCH_3$ | CH | O | S |
| $OCH_3$ | Phenyl | Methyl | Methyl | $OCH_3$ | $OCH_3$ | CH | S | S |
| OH | Phenyl | i-Propyl | Methyl | $OCH_3$ | $OCH_3$ | CH | O | O |
| $OCH_3$ | 2-Fluorophenyl | Ethyl | Methyl. | $OCH_3$ | $OCH_3$ | CH | O | O |
| $OC_2H_5$ | 3-Chlorophenyl | Propyl | Methyl | $OCH_3$ | $OCH_3$ | N | O | O |
| $ON(CH_3)_2$ | 4-Bromophenyl | i-Propyl | Methyl | $CF_3$ | $CF_3$ | CH | S. | O |
| $ON=C(CH_3)_2$ | 2-Thienyl | Methyl | Methyl | $OCF_3$ | $OCF_3$ | CH | O | S |
| $HNSO_2C_6H_5$ | 3-Thienyl | Methyl | Methyl | $CH_3$ | $CH_3$ | CH | O | O |
| NHPhenyl | 2-Furyl | Methyl | Methyl | Cl | Cl | CH | O | O |
| ONa | 3-Furyl | Methyl | Methyl | $OCH_3$ | —$OCH_2$—$CH_2$— | | S | O |
| O—$CH_2$—C≡CH | Phenyl. | Ethyl | Ethyl | $OCH_3$ | $CF_3$ | CH | O | O |
| OH | Phenyl | Propyl | Propyl | $OCH_3$ | $OCF_3$ | CH | O | S |
| $OCH_3$ | Phenyl | i-Propyl | i-Propyl | $OCH_3$ | $CH_3$ | CH | O | O |
| $OC_2H_5$ | Phenyl | Methyl | s-Butyl | $OCH_3$ | Cl | CH | S | O |
| $ON(CH_3)_2$ | 2-Methylphenyl | Methyl | Methyl | $OCH_3$ | $OCH_3$ | CH | O | O |
| $ON(CH_3)_2$ | 3-Methyoxyphenyl | Methyl | Methyl | $OCH_3$ | $OCH_3$ | CH | O | O |
| $ON=C(CH_3)_2$ | 4-Nitrophenyl | Methyl | Methyl | $OCH_3$ | $OCH_3$ | CH | O | O |
| NHPhenyl | 2-Oxazolyl | Methyl | Methyl | $CF_3$ | $CF_3$ | N | S | O |
| ONa | 4-Oxazolyl | Methyl | Propen-3-yl | $OCF_3$ | $OCF_3$ | N | O | S |
| O—$CH_2$—C≡CH | 5-Oxazolyl | Methyl | Propyn-3-yl | $CH_3$ | $CH_3$ | N | O | O |
| OH | 3-Isoxazolyl | Methyl | Cyclopentyl | Cl | Cl | N | O | O |
| $OCH_3$ | 4-Isoxazolyl | Methyl | Cyclohexyl | $OCH_3$ | —$OCH_2$—$CH_2$— | | O | O |
| $OC_2H_5$ | 5-Isoxazolyl | Methyl | Cyclopropylmethyl | $OCH_3$ | $CF_3$ | N | S | O |
| $ON(CH_3)_2$ | Phenyl | Methyl | 1-Phenylpropyl-3-yl | $OCH_3$ | $OCF_3$ | N | O | S |
| $ON=C(CH_3)_2$ | 2-Hydroxyphenyl | Methyl | Methyl | $OCH_3$ | $CH_3$ | N | O | O |
| $ONSO_2C_6H_5$ | 3-Trifluoromethylphenyl | Methyl | Methyl | $OCH_3$ | Cl | N | O | O |

TABLE-continued

| R¹ | R⁴ | R⁵ | R⁶ | R² | R³ | X | Y | Z |
|---|---|---|---|---|---|---|---|---|
| NHPhenyl | 4-Dimethylaminophenyl | Methyl | Methyl | OCH₃ | OCH₃ | CH | S | O |
| ONa | 2-Imidazolyl | Ethyl | Methyl | OCH₃ | OCH₃ | CH | S | S |
| O—CH₂—C≡CH | 4-Imidazolyl | Propyl | Methyl | OCH₃ | OCH₃ | N | S | S |
| OH | 3-Pyrazolyl | i-Propyl | Methyl | CF₃ | CF₃ | CH | O | S |
| OCH₃ | 4-Pyrazolyl | Methyl | Methyl | OCF₃ | OCF₃ | CH | O | O |
| OC₂H₅ | Phenyl | Methyl | Trifluoroethyl | CH₃ | CH₃ | CH | O | O |
| ON(CH₃)₂ | Phenyl | Methyl | Benzyl | Cl | Cl | CH | O | O |
| ON(CH₃)₂ | Phenyl | Methyl | 2-Methoxyethyl | OCH₃ | —OCH₂—CH₂— | | S | O |
| ON=C(CH₃)₂ | Phenyl | Methyl | 3-Methoxycarbonylpropyl | OCH₃ | CF₃ | N | S | S |
| NH-Phenyl | 2-Pyridyl | Methyl | 2-Chloroethyl | OCH₃ | OCF₃ | N | S | S |
| ONa | 3-Pyridyl | Methyl | Methyl | OCH₃ | CH₃ | N | O | O |
| O—CH₂—C≡CH | 4-Pyridyl | Methyl | Methyl | OCH₃ | Cl | N | O | O |

The compounds I and the herbicides containing them and their environmentally compatible salts of alkali metals and alkaline earth metals ensure very good control of weeds and grass weeds in crops such as wheat, rice and corn, soybean and cotton, without damaging the crops, an effect which occurs in particular at low application rates.

They may be applied, for example, in the form of directly sprayable solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

The compounds I are suitable in general for the preparation of directly sprayable solutions, emulsions, pastes or oil dispersions. Suitable inert additives include mineral oil fractions having a medium to high boiling point, such as kerosine or diesel oil, and coal tar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersable granules by adding water. For the preparation of emulsions, pastes or oil dispersions, the substrates [sic] as such are dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil and which are suitable for dilution with water.

Suitable surfactants are alkali metal, alkaline earth metal and ammonium salts of aromatic sulfonic acids, for example ligninsulfonic, phenolsulfonic, naphthalenesulfonic and dibutylnaphthalenesulfonic acid, and of fatty acids, alkanesulfonates, alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalene sulfonic acids with phenol and formaldehyde, polyoxyethylene octylphenyl ether, ethoxylated isooctyl-, octyl- or nonylphenyl, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene [lacuna], lauryl alcohol polyglycol ether acetate, sorbitol esters, lignin sulfite waste liquors or methyl cellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The formulations contain in general from 0.01 to 95, preferably from 0.5 to 90%, by weight of active ingredient. The active ingredients are used in the purity of from 90 to 100%, preferably from 95 to 100% (according to the NMR spectrum).

Examples of formulations are:

I. 20 parts by weight of compound No. 2.1 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of compound No. 2.1 are dissolved in a mixture which consists of 40 parts by weight of cyclohexanone, 30 parts by weight of isobutanol, 20 parts by weight of the adduct of 7 mol Of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of active ingredient No. 2.1 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 2.1 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture into 20,000 parts by weight of water, a spray liquor which contains 0.1% by weight of the active ingredient is obtained.

3 parts by weight of active ingredient No. 2.1 are mixed with 97 parts by weight of finely divided kaolin. A dusting agent which contains 3% by weight of the active ingredient is obtained in this manner.

VI. 20 parts by weight of active ingredient No. 2.1 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

Application can be carried out by the preemergence or postemergence method. If the active ingredients are less well tolerated by certain crops, it is possible to use application methods in which the herbicides are sprayed with the aid of the sprayers so that the leaves of the sensitive crops are as far as possible not affected while the active ingredients reach the leaves of undesirable plants growing underneath or the uncovered soil surface (post-directed, lay-by).

The application rates of active ingredient are from 0.001 to 5, preferably from 0.01 to 2, kg/ha of active ingredient (a.i.), depending on the aim of control, the season, the target plants and the stage of growth.

In view of the versatility of the application methods, the novel compounds or the agents containing them can be used in a further number of crops for eliminating undesirable plants. Examples of suitable crops are the following:

*Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum (Gossypium arboreum, Gossypium herbaceum, Gossypium vitifolium), Gossypium hirsutum (Gossypium arboreum, Gossypium, [sic] herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N. rustica), Olea europaea, Oryza sativa, Phaseolus lunatus, Phaseolus vulgaris, Picea abies, Pinus spp., P, isum [sic] sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

The compounds of the formula I can influence virtually all development stages of a plant in different ways and are therefore used as growth regulators. The diversity of action of the plant growth regulators depends in particular a) on the plant species and variety, b) on the time of application, based on the state of development of the plants and on the season c) on the place of application and application method (for example seed dressing, soil treatment, foliar application or trunk injection in the case of trees), d) on climatic factors, for example temperature and amount of precipitation, as well as length of day and light intensity, e) on the soil characteristics (including fertilizer application), f) on the formulation or application form of the active ingredient and finally g) on the concentration of active ingredient used.

From the many different potential applications of the plant growth regulators of the formula I in plant cultivation, in agriculture and in horticulture, some are mentioned below.

A. With the compounds which can be used according to the invention, it is possible greatly to inhibit the vegetative growth of the plants, which is evident in particular from a reduction in the growth in length.

Accordingly, the treated plants exhibit stunted growth; moreover, a darker leaf coloration is observed.

A reduced intensity of the growth of grasses and crops susceptible to lodging, such as cereals, corn, sunflowers and soybean, proves advantageous in practice. Shortening and strengthening of the stems reduce or eliminate the danger of lodging of plants under unfavorable weather conditions prior to harvesting.

The use of growth regulators for inhibiting the growth in length and for changing the time of ripening in the case of cotton is also important. This permits completely mechanized harvesting of this important crop.

In the case of fruit trees and other trees, pruning costs can be saved by means of the growth regulators. Moreover, the alternation of fruit trees can be broken by means of growth regulators.

By using growth regulators, it is also possible to increase or inhibit the lateral branching of the plants. This is of interest when, for example in the case of tobacco plants, the formation of side shoots is to be inhibited in favor of foliar growth.

Growth regulators can also be used for considerably increasing the resistance to frost, for example in the case of winter rape. On the one hand, the growth in length and the development of foliage and plant mass which is too luxurious (and therefore particularly susceptible to frost) are inhibited. On the other hand, after sowing and prior to the onset of the winter frost, the young rape plants are held back in the vegetative stage of development in spite of favorable growth conditions. This also eliminates the danger of frost for plants which tend to exhibit premature cessation of inhibition of blooming and to grow over into the generative phase. In other crops too, for example winter cereals, it is advantageous if, through treatment with the novel compounds in the fall, the stocks are well tillered but do not start the winter with too luxurious a growth. A greater sensitivity to frost and—owing to the relatively small foliage or plant mass—attack by various diseases (for example fungal disease) can thus be prevented.

B. The growth regulators can be used to achieve high yields of both plant parts and plant ingredients. For example, it is possible to induce the growth of larger amounts of buds, flowers, leaves, fruits, seed kernels, roots and tubers, to increase the content of sugar in sugarbeets, sugar cane and citrus fruits, to increase the protein content of cereals or soybean or to stimulate rubber trees to produce greater latex flow.

The compounds of the formula I can result in higher yields by intervening in the plant metabolism or by promoting or inhibiting vegetative and/or generative growth.

C. Finally, plant growth regulators can be used both for shortening and lengthening the stages of development and for accelerating or slowing down the ripening of the harvested plant parts before or after harvesting.

For example, facilitating harvesting, which is made possible by concentrated dropping or a reduction in the adhesion to a tree in the case of citrus fruits, olives or other species and varieties of pomes, drupes and indehiscent fruit, is of commercial interest. The same mechanism, ie. promotion of the formation of abscission tissue between fruit or leaf and stem part of the plant is also essential for readily controllable defoliation of crops such as cotton.

D. The growth regulators can furthermore reduce the water consumption of plants. By using the novel substances, it is possible to reduce the intensity of irrigation and hence to carry out more economical farming because, inter alia, the extent of opening of the stomata is reduced, a thicker epidermis and cuticle are formed, the root penetration of the soil is improved and the microclimate in the plant stock is favorably influenced by more compact growth.

Compounds I are particularly suitable for shortening the stems of crops such as barley, rape and wheat.

The active ingredients of the formula I which are to be used according to the invention can be fed to the crops both via the seed (as seed dressing) and via the soil, ie. through the roots and—particularly preferably—via the foliage by spraying.

The application rate of active ingredient is not critical, owing to the high tolerance by plants. The optimum application rate varies depending on the aim of control, the season, the target plants and the stages of growth.

In the case of seed treatment, in general from 0.001 to 50, preferably from 0.01 to 10, g of active ingredient per kilogram of seed are required.

For foliage and soil treatment, in general doses of from 0.001 to 10, preferably from 0.01 to 3, in particular from 0.01 to 0.5, kg/ha are to be considered sufficient.

In order to broaden the action spectrum and to achieve synergistic effects, the compounds of the formula I may be mixed with many members of other groups of herbicidal or growth-regulating active ingredients and applied together with them. Suitable components of the mixture are, for example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2 position, quinoline carboxylic acid derivatives, imidazolinones, sulfonamides, sulfonylureas, aryloxy- and heteroaryloxyphenoxy-propionic acids and their salts, esters and amides and others.

It may also be useful to apply the compounds of the formula I, alone or in combination with other herbicides, also as a mixture with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

DESCRIPTION OF THE PREFERRED EMBODIMENTS

SYNTHESIS EXAMPLES

Synthesis of compounds of the general formula VI

Example 1

Methyl 3-methoxy-3-(3-methoxyphenyl)-2-hydroxybutyrate 19.5 g (88 mmol) of methyl 3-(3-methoxyphenyl)-2,3-epoxybutyrate are dissolved in 200 ml of absolute methanol, and 0.1 ml of boron trifluoride etherate is added. Stirring is carried out for 12 hours at room temperature and the solvent is distilled off. The residue is taken up in ethyl acetate and the solution is washed with sodium bicarbonate solution and water and dried over sodium sulfate. After the solvent has been distilled off, 21.1 g of a slightly yellow oil remain.

Yield: 94% (diastereomer mixture 1:1)

Example 2

Methyl 3-benzyloxy-3-phenyl-2-hydroxybutyrate 9.6 g (50 mmol) of methyl 3-phenyl-2,3-epoxybutyrate are dissolved in 150 ml of benzyl alcohol, and 0.5 ml of concentrated sulfuric acid is added. Stirring is carried out for 6 hours at 50° C. and the mixture is allowed to cool to room temperature. After neutralization with sodium bicarbonate solution, the excess benzyl alcohol is distilled off under greatly reduced pressure 0 and the residue is purified by flash chromatography over silica gel using 9:1 n-hexane/ethyl acetate. After the solvent has been distilled off, 6.5 g of a colorless oil remain.

Yield: 43% (diasteromer mixture 3:2)

All the compounds stated in Table 1 are prepared similarly:

TABLE 1

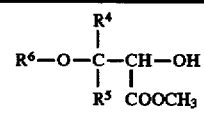

Intermediates of the formula VI where $R^1$ is $CH_3$

| No. | $R^6$ | $R^4$ | $R^5$ | DR* | Mp. [°C.] |
|---|---|---|---|---|---|
| 1.1 | Methyl | 3-Methoxyphenyl | Methyl | 1:1 | oil |
| 1.2 | Benzyl | Phenyl | Methyl | 3:2 | oil |
| 1.3 | Methyl | 2-Fluorophenyl | Methyl | 1:1 | oil |
| 1.4 | Methyl | 4-i-Propylphenyl | Methyl | | |
| 1.5 | Methyl | 2-Methylphenyl | Methyl | 2:1 | oil |
| 1.6 | Methyl | 3-Methylphenyl | Methyl | | |
| 1.7 | Methyl | 4-Methylphenyl | Methyl | 3:2 | oil |
| 1.8 | Methyl | 3-Nitrophenyl | Methyl | | |
| 1.9 | Methyl | 4-Bromophenyl | Methyl | 3:1 | oil |
| 1.10 | Methyl | 2-Furyl | Methyl | | |
| 1.11 | Methyl | 3-Furyl | Methyl | | |
| 1.12 | Methyl | 2-Thienyl | Methyl | | |
| 1.13 | Methyl | 3-Thienyl | Methyl | | |
| 1.14 | Methyl | 2-Pyridyl | Methyl | | |

TABLE 1-continued $$R^6-O-\underset{\underset{COOCH_3}{|}}{\overset{\overset{R^4}{|}}{C}}-CH-OH$$
$$\phantom{R^6-O-}R^5$$

Intermediates of the formula VI where $R^1$ is $CH_3$

| No. | $R^6$ | $R^4$ | $R^5$ | DR* | Mp. [°C.] |
|---|---|---|---|---|---|
| 1.15 | Methyl | 3-Pyridyl | Methyl | | |
| 1.16 | Methyl | 4-Pyridyl | Methyl | | |
| 1.17 | Methyl | 2-Thiazolyl | Methyl | | |
| 1.18 | Methyl | 3-Isoxazolyl | Methyl | | |
| 1.19 | Methyl | 4-Imidazolyl | Methyl | | |
| 1.20 | Methyl | 2-Pyrazolyl | Methyl | | |
| 1.21 | Methyl | 4-Chlorophenyl | Methyl | 2:1 | oil |
| 1.22 | Benzyl | 3-Methylphenyl | Methyl | 1:1 | oil |
| 1.23 | Methyl | 4-Fluorophenyl | Methyl | 1:1 | oil |
| 1.24 | Benzyl | 4-Bromophenyl | Methyl | 1:1 | oil |
| 1.25 | Benzyl | 4-Chlorophenyl | Methyl | 3:2 | oil |
| 1.26 | Benzyl | 4-Fluorophenyl | Methyl | 1:1 | oil |
| 1.27 | Methyl | Phenyl | Ethyl | 1:1 | oil |
| 1.28 | Methyl | 3-Nitrophenyl | Methyl | 2:1 | oil |
| 1.29 | Ethyl | 4-Methylphenyl | Methyl | 1:1 | oil |
| 1.30 | Benzyl | 4-Methylphenyl | Methyl | 1:1 | oil |
| 1.31 | Benzyl | Phenyl | Ethyl | 1:0 | oil |
| 1.32 | 4-Fluorobenzyl | Phenyl | Methyl | 1:1 | oil |

*Diastereomer Ratio

Synthesis of compounds of the general formula I:

Example 3

Methyl 3-benzyloxy-3-phenyl-2-(4,6-dimethoxypyrimidin-2-yloxy)butyrate 3 g (10 mmol) of methyl 3-benzyloxy-3-phenyl-2-hydroxybutyrate (compound 1.1) are dissolved in 40 ml of dimethylformamide, and 0.3 g (12 mmol) of sodium hydride are added. Stirring is carried out for 1 hour, after which 2.2 g (10 mmol) of 4,6-dimethoxy-2-methylsulfonylpyrimidine are added. After stirring has been carried out for 24 hours at room temperature, hydrolysis is effected carefully with 10 ml of water, the pH is brought to 5 with acetic acid and the solvent is distilled off under greatly reduced pressure. The residue is taken up in 100 ml of ethyl acetate, washed with water and dried over sodium sulfate and the solvent is distilled off. 10 ml of methyl tert-butyl ether are added to the residue and the precipitate formed is filtered off with suction. After drying, 2.4 g of a white powder remain.

Yield: 55% (diastereomer mixture 1:1) Mp.: 115°–117° C.

Example 4

3-Benzyloxy-3-phenyl-2-(4,6-dimethoxypyrimidin-2-yloxy)butyric acid 1.4 g (3 mmol) of methyl 3-benzyloxy-3-phenyl-2-(4,6-dimethoxypyrimidin-2-yloxy)butyrate (Example 3) are dissolved in 20 ml of methanol and 20 ml of tetrahydrofuran, and 3.7 g of 10% strength NaOH solution are added. Stirring is carried out for 6 hours at 60° C. and for 12 hours at room temperature, the solvent is distilled off under reduced pressure and the residue is taken up in 100 ml of water. Extraction is now carried out with ethyl acetate to remove unconverted ester. The aqueous phase is then brought to pH 1–2 with dilute hydrochloric acid and is extracted with ethyl acetate. After drying has been carried out over magnesium sulfate and the solvent has been distilled off, a little acetone is added to the residue and the precipitate formed is filtered off with suction. After drying, 1.2 g of a white powder remain.

Yield: 88% Mp.: 165° C. (decomposition, diastereomer mixture 3:2)

Example 5

Methyl 3-benzyloxy-3-phenyl-2-(4,6-dimethoxypyrimidin-2-ylthio)-butyrate 11 g (25 mmol) of methyl 3-benzyloxy-3-phenyl-2-hydroxybutyrate (compound 1.1) are dissolved in 50 ml of dichloromethane, 3 g (30 mmol) of triethylamine are added and 3.2 g (28 mmol) of methanesulfonyl chloride are added dropwise while stirring. Stirring is continued for 2 hours at room temperature, and the mixture is washed with water, dried over magnesium sulfate and evaporated down under reduced pressure. The residue is taken up in dimethylformamide and the solution is added dropwise at 0° C. to a suspension of 12.9 g (75 mmol) of 4,6-dimethoxypyrimidine-2-thiol and 8.4 g (100 mmol) of sodium bicarbonate in 100 ml of dimethylformamide. After stirring has been carried out for 2 hours at room temperature and for a further 2 hours at 60° C., the mixture is poured onto 1 l of ice water and the resulting precipitate is filtered off with suction. After drying, 3.2 g of a white powder remain.

Yield: 29% (diastereomer mixture 1:1)

The compounds stated in Table 2 were prepared similarly to the above examples.

TABLE 2

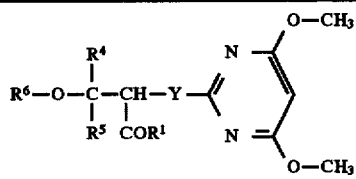

| No. | $R^6$ | $R^4$ | $R^5$ | Y | $R^1$ | Diastereomers | Mp. (°C.) |
|---|---|---|---|---|---|---|---|
| 2.1 | Benzyl | Phenyl | Methyl | O | $OCH_3$ | 1:1 | 115–117 |
| 2.2 | Benzyl | Phenyl | Methyl | O | OH | 3:2 | 165 (decomp.) |
| 2.3 | Benzyl | Phenyl | Methyl | S | $OCH_3$ | 1:1 | |
| 2.4 | Benzyl | Phenyl | Methyl | S | OH | | |
| 2.5 | Methyl | 2-Fluorophenyl | Methyl | O | $OCH_3$ | 1:1 | 126–128 |
| 2.6 | Methyl | 2-Fluorophenyl | Methyl | O | OH | 2:1 | 185–186 |

TABLE 2-continued

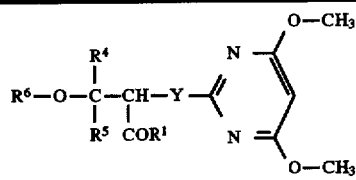

| No. | R⁶ | R⁴ | R⁵ | Y | R¹ | Diastereomers | Mp. (°C.) |
|---|---|---|---|---|---|---|---|
| 2.7 | Methyl | 3-Methoxyphenyl | Methyl | O | OCH₃ | 1:0 (5:1) | 131–132 (93–95) |
| 2.8 | Methyl | 3-Methoxyphenyl | Methyl | O | OH | 1:0 | 187–189 |
| 2.9 | Methyl | 4-i-Propylphenyl | Methyl | O | OCH₃ | | |
| 2.10 | Methyl | 4-i-Propylphenyl | Methyl | O | OH | | |
| 2.11 | Methyl | 2-Methylphenyl | Methyl | O | OCH₃ | 3:1 | 122–124 |
| 2.12 | Methyl | 2-Methylphenyl | Methyl | O | OH | 1:1 | 135–137 |
| 2.13 | Methyl | 3-Methylphenyl | Methyl | O | OCH₃ | 1:1 | 105–110 |
| 2.14 | Methyl | 3-Methylphenyl | Methyl | O | OH | 1:1 | 130–132 |
| 2.15 | Methyl | 4-Methylphenyl | Methyl | O | OCH₃ | 1:1 | 99–102 |
| 2.16 | Methyl | 4-Methylphenyl | Methyl | O | OH | 1:1 | 145–147 |
| 2.17 | Methyl | 4-Bromophenyl | Methyl | O | OCH₃ | 1:0 | 148–150 |
| 2.18 | Methyl | 4-Bromophenyl | Methyl | O | OH | 1:0 | 189–190 |
| 2.19 | Methyl | 2-Furyl | Methyl | O | OCH₃ | | |
| 2.20 | Methyl | 2-Furyl | Methyl | O | OH | | |
| 2.21 | Methyl | 3-Furyl | Methyl | O | OCH₃ | | |
| 2.22 | Methyl | 3-Furyl | Methyl | O | OH | | |
| 2.23 | Methyl | 2-Thienyl | Methyl | O | OCH₃ | | |
| 2.24 | Methyl | 2-Thienyl | Methyl | O | OH | | |
| 2.25 | Methyl | 2-Pyridyl | Methyl | O | OCH₃ | 2:1 | oil |
| 2.26 | Methyl | 2-Pyridyl | Methyl | O | ONa | | 175–176 |
| 2.27 | Methyl | 3-Pyridyi | Methyl | O | OCH₃ | | |
| 2.28 | Methyl | 3-Pyridyl | Methyl | O | OH | | |
| 2.29 | Methyl | 4-Pyridyl | Methyl | O | OCH₃ | | |
| 2.30 | Methyl | 4-Pyridyl | Methyl | O | OH | | |
| 2.31 | Methyl | 3-Chlorophenyl | Methyl | O | OCH₃ | | |
| 2.32 | Methyl | 3-Chlorophenyl | Methyl | O | OH | | |
| 2.33 | Methyl | 2-Thiazolyl | Methyl | O | OCH₃ | | |
| 2.34 | Methyl | 2-Thiazolyl | Methyl | O | OH | | |
| 2.35 | Methyl | 3-Isoxazolyl | Methyl | O | OCH₃ | | |
| 2.36 | Methyl | 3-Isoxazolyl | Methyl | O | OH | | |
| 2.37 | Methyl | 4-Imidazolyl | Methyl | O | OCH₃ | | |
| 2.38 | Methyl | 4-Imidazolyl | Methyl | O | OH | | |
| 2.39 | Methyl | 2-Pyrazolyl | Methyl | O | OCH₃ | | |
| 2.40 | Methyl | 2-Pyrazolyl | Methyl | O | OH | | |
| 2.41 | Benzyl | 4-Chlorophenyl | Methyl | O | OCH₃ | 1:1 | 112–114 |
| 2.42 | Benzyl | 4-Chlorophenyl | Methyl | O | OH | | |
| 2.43 | i-Propyl | 2-Fluorophenyl | Methyl | O | OCH₃ | 4:1 | 115–120 |
| 2.44 | i-Propyl | 2-Fluorophenyl | Methyl | O | OH | 2:1 | 143–145 |
| 2.45 | Methyl | 4-Fluorophenyl | Methyl | O | OCH₃ | 1:1 | 122–125 |
| 2.46 | Methyl | 4-Fluorophenyl | Methyl | O | OH | 3:1 | 170–172 |
| 2.47 | Benzyl | 3-Methylphenyl | Methyl | O | OCH₃ | 1:1 | 94–95 |
| 2.48 | Benzyl | 3-Methylphenyl | Methyl | O | OH | 1:1 | 154–156 |
| 2.49 | Methyl | 4-Chlorophenyl | Methyl | O | OCH₃ | 1:1 | 125–127 |
| 2.50 | Methyl | 4-Chlorophenyl | Methyl | O | OH | 5:1 | 206–207 |
| 2.51 | Methyl | Phenyl | Ethyl | O | OCH₃ | 1:0 | 95–100 |
| 2.52 | Methyl | Phenyl | Ethyl | O | OH | 1:0 | 140–142 |
| 2.53 | Benzyl | 4-Fluorophenyl | Methyl | O | OCH₃ | 1:1 | 95–98 |
| 2.54 | Benzyl | 4-Fluorophenyl | Methyl | O | OH | 4:1 | 153–154 |
| 2.55 | 4-Fluorobenzyl | Phenyl | Methyl | O | OCH₃ | 1:0 | 152–153 |
| 2.56 | 4-Fluorobenzyl | Phenyl | Methyl | O | OH | 7:3 | 160–162 |
| 2.57 | 4-Bromobenzyl | Phenyl | Methyl | O | OCH₃ | 9:1 | 158–160 |
| 2.58 | 4-Bromobenzyl | Phenyl | Methyl | O | OH | 1:0 | 203–204 |
| 2.59 | Benzyl | 2-Fluorophenyl | Methyl | O | OCH₃ | 1:0 | 129–130 |
| 2.60 | Benzyl | 2-Fluorophenyl | Methyl | O | OH | 1:0 | 200–201 |
| 2.61 | Benzyl | 4-Bromophenyl | Methyl | O | OCH₃ | 1:1 | 78–79 |
| 2.62 | Benzyl | 4-Bromophenyl | Methyl | O | OH | 1:1 | 156–158 |
| 2.63 | Benzyl | 4-Methylphenyl | Methyl | O | OCH₃ | 1:1 | oil |
| 2.64 | Benzyl | 4-Methylphenyl | Methyl | O | OH | 4:1 | 158–159 |
| 2.65 | Benzyl | Phenyl | Ethyl | O | OCH₃ | 1:0 | 110–112 |
| 2.66 | Benzyl | Phenyl | Ethyl | O | OH | 1:0 | 92–93 |
| 2.67 | Ethyl | 4-Methylphenyl | Methyl | O | OCH₃ | 1:0 | 117–119 |
| 2.68 | Ethyl | 4-Methylphenyl | Methyl | O | OH | 1:1 | oil |
| 2.69 | Methyl | 2-Furyl | H | O | OCH₃ | 1:1 | oil |
| 2.70 | Methyl | 2-Furyl | H | O | OH | 1:1 | oil |
| 2.71 | 4-Chlorobenzyl | Phenyl | Methyl | O | OCH₃ | 1:0 | 172–174 |
| 2.72 | 4-Chlorobenzyl | Phenyl | Methyl | O | OH | 1:0 | 60–61 |
| 2.73 | 2-Butyl | 4-Bromophenyl | Methyl | O | OCH₃ | — | 104–106 |
| 2.74 | 2-Butyl | 4-Bromophenyl | Methyl | O | OH | 1:0 | 153–154 |

TABLE 2-continued $$R^6-O-\underset{\underset{COR^1}{|}}{\overset{\overset{R^4}{|}}{C}}-CH-Y-\left\langle\begin{array}{c}N=\\\\N=\end{array}\right.\begin{array}{c}O-CH_3\\\\O-CH_3\end{array}$$

| No. | $R^6$ | $R^4$ | $R^5$ | Y | $R^1$ | Diastereomers | Mp. (°C.) |
|---|---|---|---|---|---|---|---|
| 2.75 | n-Propyl | 4-Fluorophenyl | Methyl | O | $OCH_3$ | 9:1 | 119–120 |
| 2.76 | n-Propyl | 4-Fluorophenyl | Methyl | O | OH | 9:1 | 104–105 |
| 2.77 | Methyl | 3-Nitrophenyl | Methyl | O | $OCH_3$ | 1:1 | 101–102 |
| 2.78 | Methyl | 3-Nitrophenyl | Methyl | O | OH | 1:1 | 165–172 |
| 2.79 | Methyl | 4-Trifluorophenyl | Methyl | O | $OCH_3$ | 1:0 | 112–113 |
| 2.80 | Methyl | 4-Trifluorophenyl | Methyl | O | OH | 4:1 | 68–70 |
| 2.81 | Methyl | 3-Thienyl | H | O | $OCH_3$ | 1:1 | 80–82 |
| 2.82 | Methyl | 3-Thienyl | H | O | OH | 1:1 | oil |
| 2.83 | 4-Chlorobenzyl | Phenyl | Methyl | O | $OCH_3$ | 0:1 | 112–113 |
| 2.84 | 4-Chlorobenzyl | Phenyl | Methyl | O | $OCH_3$ | 0:1 | 60–61 |
| 2.85 | Methyl | Phenyl | Ethyl | O | $OCH_3$ | 1:3 | 125–130 |
| 2.86 | Methyl | Phenyl | Ethyl | O | OH | 0:1 | 133–135 |
| 2.87 | Benzyl | 3-Methoxyphenyl | Methyl | O | $OCH_3$ | 3:1 | 86–87 |
| 2.88 | Benzyl | 3-Methoxyphenyl | Methyl | O | OH | 1:0 | 155 |
| 2.89 | Benzyl | 3-Methoxyphenyl | Methyl | O | OH | 0:1 | 138–14Q |
| 2.90 | 2-Phenylethyl | Phenyl | Methyl | O | OH | 1:0 | 147–149 |
| 2.91 | Methyl | 3-Furyl | H | O | $OCH_3$ | 1:1 | oil |
| 2.92 | Methyl | 3-Furyl | H | O | OH | 1:1 | 131–135 |
| 2.93 | 3-$CF_3$—benzyl | Phenyl | Methyl | O | $OCH_3$ | 2:1 | 151–152 |
| 2.94 | 3-$CF_3$—benzyl | Phenyl | Methyl | O | OH | 1:1 | oil |
| 2.95 | 2-Fluorobenzene | Phenyl | Methyl | O | $OCH_3$ | 2:1 | 170–173 |
| 2.96 | 2-Fluorobenzene | Phenyl | Methyl | O | OH | 1:0 | 160–162 |
| 2.97 | 2-Fluorobenzene | Phenyl | Methyl | O | OH | 1:3 | 138–141 |
| 2.98 | 3-Fluorobenzyl | Phenyl | Methyl | O | $OCH_3$ | 1:1 | 81–86 |
| 2.99 | 3-Fluorobenzyl | Phenyl | Methyl | O | OH | 4:1 | 195–197 |
| 2.100 | 3-Fluorobenzyl | Phenyl | Methyl | O | ONa | 3:1 | 250–260 |
| 2.101 | 4-Fluorobenzyl | Phenyl | Methyl | O | $OCH_3$ | 1:1 | 112–115 |
| 2.102 | 4-Fluorobenzyl | Phenyl | Methyl | O | OH | | |

Use examples:

The herbicidal action of the 3-(het)arylcarboxylic acid derivatives of the general formula I could be demonstrated by greenhouse experiments:

The culture vessels used were plastic flowerpots containing loamy sand with about 3.0% of humus as a substrate. The seeds of the test plant were sown separately according to species.

In the preemergence treatment, the active ingredients suspended or emulsified in water were applied directly after sowing by means of finely distributing nozzles. The vessels were lightly sprinkler-irrigated in order to promote germination and growth and were then covered with transparent plastic covers until the plants had begun to grow. This covering ensures uniform germination of the test plants, unless this has been adversely affected by the active ingredients.

For the postemergence application, the test plants are grown to a height of growth of from 3 to 15 cm, depending on the form of growth, before being treated with the active ingredients suspended or emulsified in water. For this purpose, the test plants are either sown directly and grown in the same vessels or first grown separately as seedlings and transplanted into the test vessels a few days before the treatment. The application rate for the postemergence treatment is 0.125 or 0.06 kg/ha of a.i.

The plants were kept at 10° to 25° C. or 20° to 35° C., according to species. The experimental period is extended over from 2 to 4 weeks. During this time, the plants were tended, .and their reaction to the individual treatments was evaluated.

Evaluation was based on a scale from 0 to 100. 100 means no emergence of the plant or complete destruction of at least the aboveground parts and 0 means no damage or normal course of growth.

The plants used in the greenhouse experiments consisted of the following species:

| Botanical Name | Common Name | Abbreviation |
|---|---|---|
| Gossypium hirsutum | Cotton | GOSHI |
| Oryza sativa | Rice | ORYSA |
| Triticum aestivum | Summer wheat | TRZAS |
| Alopecurus myosuroides | Slender foxtail | ALOMY |
| Amaranthus retroflexus | Redroot pigweed | AMARE |
| Brachiaria platyphylla | — | BRAPP |
| Chenopodium album | Common lambsquarters | CHEAL |
| Sesbania exaltata | Hemp susbania | SEBEX |
| Setaria faberii | Giant foxtail | SETFA |
| Setaria viridis | Green foxtail | SETVI |
| Solanum nigrum | Black nightshade | SOLNI |
| Veronica spp. | Speedwell species | VERSS |

The results listed in Table A show the superior herbicidal action and the better selectivity of the novel compound No. 2.2 in comparison with the comparative substance A disclosed in EP-A 409 368

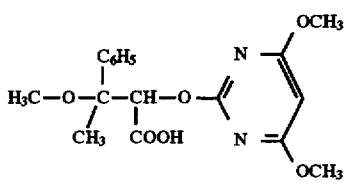

TABLE A

Examples of the control of undesirable plants and selectivity in the example crop cotton with postemergence application of 0.125 or 0.06 kg/ha of a.i. in the greenhouse.

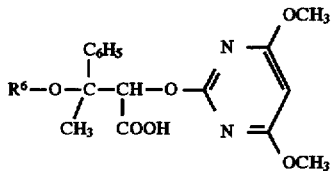

| $R^6$ Example No. Test plants | Benzyl 2.2 Damage in % | | $CH_3$ A Damage in % | |
|---|---|---|---|---|
| | 0.125 kg/ha | 0.06 kg/ha | 0.125 kg/ha | 0.06 kg/ha |
| GOSHI | 10 | 5 | 35 | 20 |
| SEFTA | 100 | 100 | 75 | 70 |
| SETVI | 100 | 98 | 80 | 60 |
| AMARE | 98 | 98 | 100 | 75 |
| SOLNI | 100 | 100 | 98 | 90 |

At application rates of 5 kg/ha to 0.25 kg/ha, compounds No. 2.84, 2.16, 2.52, 2.86 and 2.25 showed good herbicidal activity. Compounds No. 2.84 and 2.16 simultaneously showed very good selectivity in the example crop cotton. In addition, Example No. 2.16 was also selective in rice. Example 2.52 was well tolerated by the crop summer wheat.

We claim:

1. A 3-(het)arylcarboxylic acid derivative of the formula I

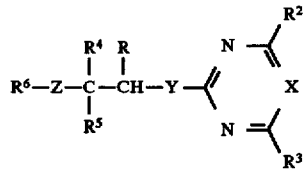

where R is formyl, $CO_2H$ or a radical hydrolyzable to COOH and $R_2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{14}$, where $R^{14}$ is hydrogen or, together with $R^3$, forms a 3-membered or 4-membered alkylene or alkenylene chain, in each of which a methylene group is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio or $R^3$ is linked to $R^{14}$ as stated above to form a 5-membered or 6-membered ring;

$R^4$ is phenyl or naphthyl which may be substituted by one or more, in particular one to three, of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl or $C_1$–$C_4$-alkoxycarbonyl;

a five-membered or six-membered heteroaromatic structure which contains one to three nitrogen atoms and/or one sulfur or oxygen atom and may carry one or more of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, $C_1$–$C_4$-dialkylamino, $C_1$–$C_4$-alkylcarbonyl, $C_1$–$C_4$-alkoxycarbonyl or phenyl;

$R^5$ is hydrogen, $C_1$–$C_4$-alkyl, $C_3$–$C_6$-alkenyl, $C_3$–$C_6$-alkynyl, $C_3$–$C_8$-cycloalkyl, $C_1$–$C_4$-haloalkyl, $C_1$–$C_4$-alkoxyalkyl, $C_1$–$C_4$-alkylthioalkyl or phenyl;

$R^6$ is $C_1$–$C_8$-alkyl, $C_3$–$C_6$-alkenyl, $C_3$–$C_6$-alkynyl or $C_3$–$C_8$-cycloalkyl, it being possible for these radicals to be mono- or polysubstituted in each case by: halogen, nitro, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_1$–$C_4$-alkylamino, di-$C_1$–$C_4$-alkylamino, phenyl or phenyl or phenoxy which is mono- or polysubstituted, for example mono- to trisubstituted, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

Y is sulfur or oxygen or a single bond; and

Z is sulfur or oxygen;

with the proviso that $R^6$ is not unsubstituted $C_1$–$C_4$-alkyl when $R^4$ is unsubstituted phenyl, Z is oxygen and simultaneously $R^5$ is methyl or hydrogen.

2. A 3-(het)arylcarboxylic acid derivative of the general formula I as claimed in claim 1, where R is

where $R^1$ has the following meanings:

a) hydrogen;

b) a succinylimidoxy group;

c) a 5-membered heteroaromatic structure which is bonded via a nitrogen atom, contains two or three nitrogen atoms and may carry one or two halogen atoms or one or two of the following radicals:

$C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

d) a radical

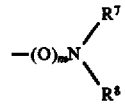

where m is 0 or 1 and $R^7$ and $R^8$, which may be identical or different, have the following meanings:

hydrogen;

$C_1$–$C_8$-alkyl, $C_3$–$C_6$-alkenyl, $C_3$–$C_6$-alkynyl or $C_3$–$C_8$-cycloalkyl, where each of these radicals may carry one to five halogen atoms or one or two of the following groups: $C_1$–$C_4$-alkoxy, $C_3$–$C_6$-alkenyloxy, $C_3$–$C_6$-alkynyloxy, $C_1$–$C_4$-alkylthio, $C_3$–$C_6$-alkenylthio, $C_3$–$C_6$-alkynylthio, $C_1$–$C_4$-haloalkoxy, $C_1$–$C_4$-alkylcarbonyl, $C_3$–$C_6$-alkenylcarbonyl, $C_3$–$C_6$-alkynylcarbonyl, $C_1$–$C_4$-alkoxycarbonyl, $C_3$–$C_6$-alkenyloxycarbonyl, $C_3$–$C_6$-alkynyloxycarbonyl, di-$C_1$–$C_4$-alkylamino, $C_3$–$C_8$-cycloalkyl, phenyl or phenyl which is monosubstituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $c_1$–$C_4$-alkylthio;

phenyl which may be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^7$ and $R^8$ together form a cyclic, optionally substituted $C_4$–$C_7$-alkylene chain or together form a cyclic, optionally substituted $C_3$–$C_6$-alkylene chain containing a heteroatom selected from the group consisting of oxygen, sulfur and nitrogen;

e) $R^1$ is furthermore a group

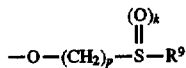

where $R^9$ is $C_1$–$C_4$-alkyl, phenyl or phenyl which is monosubstituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $C_1$–$C_4$-haloalkyl, $C_3$–$C_6$-alkenyl or $C_3$–$C_6$-alkynyl, p may be 1, 2, 3 or 4 and k may be 0, 1 or 2;

f) a radical $OR^{10}$, where $R^{10}$ is:

i) hydrogen, an alkali metal cation, one equivalent of an alkaline earth metal cation, the ammonium cation or an organic ammonium ion;

ii) $C_3$–$C_8$-cycloalkyl which may carry one to three $C_1$–$C_4$-alkyl radicals;

iii) $C_1$–$C_8$-alkyl which may carry one to five halogen atoms or one of the following radicals:

$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, phenoxy or phenylcarbonyl, where the aromatic radicals in turn may each carry one to five halogen atoms or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

iv) $C_1$–$C_8$-alkyl which may carry one to five halogen atoms and carries one of the following radicals: a 5-membered heteroaromatic structure containing one to three nitrogen atoms or a 5-membered heteroaromatic structure containing one nitrogen atom and one oxygen or sulfur atom, which may carry one to four halogen atoms or one or two of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

v) $C_2$–$C_6$-alkyl which carries one of the following radicals in the 2 position: $C_1$–$C_4$-alkoxyimino, $C_3$–$C_6$-alkenyloxyimino, $C_3$–$C_6$-haloalkenyloxyimino or benzyloxyimino;

vi) $C_3$–$C_6$-alkenyl or $C_3$–$C_6$-alkynyl, where these groups in turn may carry one to five halogen atoms;

vii) phenyl which may carry one to five halogen atoms or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

viii) a 5-membered heteroaromatic structure which has bonded via a nitrogen atom, contains one to three nitrogen atoms and may carry one or two halogen atoms or one or two of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

ix) $R^{10}$ is furthermore a group

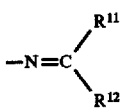

where
$R^{11}$ and $R^{12}$, may be identical or different and are each: $C_1$–$C_8$-alkyl, $C_3$–$C_6$-alkenyl, $C_3$–$C_6$-alkynyl or $C_3$–$C_8$-cycloalkyl, where these radicals may carry one $C_1$–$C_4$-alkoxy or $C_1$–$C_4$-alkylthio or one phenyl radical;
phenyl which may be substituted by one or more of the following radicals:
halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
or $R^{11}$ and $R^{12}$ together form a $C_3$–$C_{12}$-alkylene chain which may carry one to three $C_1$–$C_4$-alkyl groups;

g) or $R^1$ forms a radical

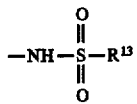

where $R^{13}$ is:
$C_1$–$C_4$-alkyl, $C_3$–$C_6$-alkenyl, $C_3$–$C_6$-alkynyl or $C_3$–$C_8$-cycloalkyl, where these radicals may carry one $C_1$–$C_4$-alkoxy or $C_1$–$C_4$-alkylthio or one phenyl radical;
phenyl which may be substituted by one to five halogen atoms or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio.

3. A 3-arylcarboxylic acid derivative of the formula I as claimed in claim 1, in which $R^4$ is phenyl which may be substituted as stated in claim 1, and the remaining substituents have the meanings stated in claim 1.

4. A 3-arylcarboxylic acid derivative of the formula I as claimed in claim 1, in which Z is oxygen, $R^4$ is phenyl which may be substituted as stated in claim 1, $R^5$ is methyl, X is CH, $R^2$ and $R^3$ are each methoxy and Y, $R^1$ and $R^6$ have the meanings stated in claim 1.

5. A 3-hetarylcarboxylic acid derivative of the formula I as claimed in claim 1, in which $R^4$ is a five- or six-membered heteroaromatic structure as claimed in claim 1 and the remaining substituents have the meanings stated in claim 1.

6. A 3-hetarylcarboxylic acid derivative of the formula I as claimed in claim 1, in which Z is oxygen, $R^4$ is a five- or six-membered heteroaromatic structure as claimed in claim 1, $R^5$ is methyl, X is CH, $R^2$ and $R^3$ are methoxy and Y, $R^1$ and $R^6$ have the meanings stated in claim 1.

7. A herbicide containing a compound of the formula I as claimed in claim 1 and conventional inert additives.

8. A method for controlling undesirable plant growth, wherein a herbicidal amount of a compound of the formula I as claimed in claim 1 is allowed to act on the plants or on their habitat.

9. An agent for influencing plant growth, containing a compound of the formula I as claimed in claim 1 and conventional inert additives.

10. A method for regulating plant growth, wherein a bioregulatory amount of a compound of the formula I as claimed in claim 1 is allowed to act on the plants or on their habitat.

11. A 3-(het)arylcarboxylic acid derivative of the formula VI

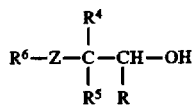  VI where R, R⁴, R⁵, R⁶ and Z have the meanings stated in claim 1, with the proviso that R⁶ is not unsubstituted alkyl when R⁴ is unsubstituted phenyl or 4-isobutylphenyl, Z is oxygen and R⁵ is simultaneously methyl or hydrogen.

12. A process for the preparation of a 3-(het)arylcarboxylic acid derivative of the formula VI

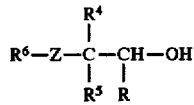  VI wherein an epoxide of the formula IV

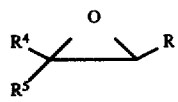  IV where R, R⁴ and R⁵ have the meanings stated in claim 1, is reacted with a compound of the formula V

where R⁶ and Z have the meanings stated in claim 1, with the proviso that R⁶ is not unsubstituted alkyl when R⁴ is unsubstituted phenyl or 4-isobutylphenyl, Z is oxygen and R⁵ is simultaneously methyl or hydrogen, if required in an inert solvent or with the addition of a suitable catalyst.

13. A process for the preparation of 3-(het)arylcarboxylic acid derivatives of the formula I as claimed in claim 1, where is oxygen wherein the 3-het(aryl)carboxylic acid derivative of the formula VI

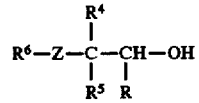  VI where the substituents have the meanings stated in claim 1, is reacted with a pyrimidyl or triazinyl derivative of the formula VII

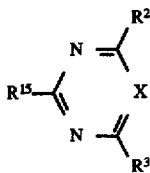  VII where R¹⁵ is halogen or R¹⁶SO₂— and R¹⁶ is $C_1$–$C_4$-alkyl, $C_1$–$C_4$-haloalkyl or phenyl, in an inert solvent in the presence of a base.

14. A process for the preparation of a 3-het(aryl)carboxylic acid derivative of the formula I as claimed in claim 1, where Y is sulfur, wherein a 3-het(aryl)carboxylic acid derivative of the formula VIII

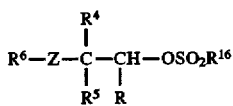  VI where the substituents have the meanings stated in claim 12, is reacted with a pyrimidyl—or triazinylthiol of the formula IX

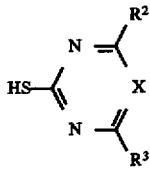  IX where R², R³ and X have the meanings stated in claim 1, with the proviso that R⁶ is not unsubstituted alkyl when R⁴ is unsubstituted phenyl or 4-isobutylphenyl, Z is oxygen and R⁵ is simultaneously methyl or hydrogen.

* * * * *

UNITED STATES PATENT AND TRADEMARK OFFICE
CERTIFICATE OF CORRECTION

PATENT NO.: 5,703,017

DATED: December 30, 1997

INVENTOR(S): BAUMANN et al.

It is certified that error appears in the above-identified patent and that said Letters Patent is hereby corrected as shown below:

In the Abstract, cover page item [57], line 29, "$C_3$-$C_4$-" should be -- $C_3$-$C_8$- --.

Column 24, claim 2, line 65, "$_{C1}$-$C_4$-alkylthio" should be --$C_1$-$C_4$-alkylthio--.

Column 25, claim 2, line 26, "Which" should be --which--.

Signed and Sealed this

Third Day of March, 1998

BRUCE LEHMAN

*Attest:*

*Attesting Officer*  *Commissioner of Patents and Trademarks*

UNITED STATES PATENT AND TRADEMARK OFFICE
CERTIFICATE OF CORRECTION

PATENT NO.       : 5,703,017
APPLICATION NO.  : 08/537843
DATED            : December 30, 1997
INVENTOR(S)      : Ernst Baumann et al.

Page 1 of 1

It is certified that error appears in the above-identified patent and that said Letters Patent is hereby corrected as shown below:

Column 27, line 35: insert --Y-- before the phrase "is oxygen"

Signed and Sealed this

Eleventh Day of September, 2007

JON W. DUDAS
*Director of the United States Patent and Trademark Office*